United States Patent [19]

Hall et al.

[11] Patent Number: 4,656,185
[45] Date of Patent: Apr. 7, 1987

[54] 7-OXABICYCLOHEPTANE SUBSTITUTED AMINOALKYL AMIDE PROSTAGLANDIN ANALOGS

[75] Inventors: Steven E. Hall, Ewing Township, Mercer County; Masami Nakane, Hopewell, both of N.J.

[73] Assignee: E. R. Squibb & Sons, Inc., Princeton, N.J.

[21] Appl. No.: 804,729

[22] Filed: Dec. 5, 1985

[51] Int. Cl.[4] .................. C07D 493/08; C07D 405/14; A01K 31/34; A01K 31/41
[52] U.S. Cl. .................... 514/382; 514/469; 548/252; 549/463
[58] Field of Search ........................ 548/252; 549/463; 514/382, 469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,617 | 6/1984 | Nakane et al. | 424/285 |
| 4,526,901 | 7/1985 | Nakane | 514/469 |

FOREIGN PATENT DOCUMENTS

| | | |
|---|---|---|
| 0043292 | 8/1982 | European Pat. Off. . |
| 0082646 | 6/1983 | European Pat. Off. . |
| 2039909 | 8/1980 | United Kingdom . |

Primary Examiner—Robert Gerstl
Attorney, Agent, or Firm—Lawrence S. Levinson; Burton Rodney

[57] ABSTRACT

7-Oxabicycloheptane substituted diacid diamide prostaglandin analogs are provided having the structural formula

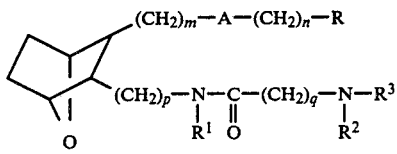

wherein m is 0 to 4; A is —CH=CH— or —CH$_2$—CH$_2$—; n is 1 to 5; R is CO$_2$H, CO$_2$alkyl, CO$_2$alkali metal, CO$_2$polyhydroxyamine salt, —CH$_2$OH

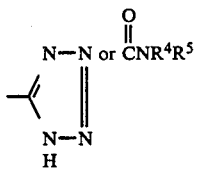

wherein R$^4$ and R$^5$ are the same or different and are H, lower alkyl, hydroxy, lower alkoxy or aryl, at least one of R$^4$ and R$^5$ being other than hydroxy and lower alkoxy; p is 1 to 4; R$^1$ is H or lower alkyl; q is 1 to 12; R$^2$ and R$^3$ are the same or different and are H, lower alkly, lower alkenyl, lower alkynyl, aryl, arylalkyl, lower alkoxy, aralkyloxy, cycloalkyl or cycloalkylalkyl.

The compounds are cardiovascular agents useful, for example, in the treatment of thrombotic disease.

16 Claims, No Drawings

7-OXABICYCLOHEPTANE SUBSTITUTED AMINOALKYL AMIDE PROSTAGLANDIN ANALOGS

DESCRIPTION OF THE INVENTION

The present invention relates to 7-oxabicycloheptane substituted aminoalkyl amide prostaglandin analogs which are cardiovascular agents useful, for example, in the treatment of thrombotic disease. These compounds have the structural formula

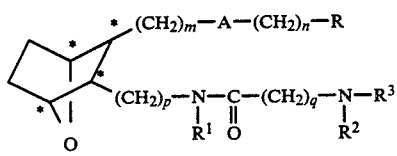

including all stereoisomers thereof, and physiologically acceptable acid-addition salts thereof, wherein m is 0 to 4; A is $-CH=CH-$ or $-CH_2-CH_2-$; n is 1 to 5; R is $CO_2H$, $CO_2$alkyl, $CO_2$alkali metal, $CO_2$polyhydroxyamine salt, $-CH_2OH$,

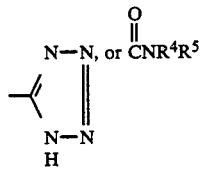

wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; q is 1 to 12; and $R^2$ and $R^3$ may be the same or different and are H, lower alkyl, lower alkenyl, lower alkynyl, aryl, arylalkyl, cycloalkyl or cycloalkylalkyl.

The term "lower alkyl" or "alkyl" as employed herein alone or as part of another group includes both straight and branched chain hydrocarbon radicals of from 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent, or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cycododecyl, any of which groups may be substituted with 1 or 2 halogens, 1 or 2 lower alkyl groups 1 or 2 lower alkoxy groups. 1 or 2 hydroxy groups, 1 or 2 alkylamino groups, 1 or 2 alkanoylamino groups, 1 or 2-arylcarbonylamino groups, 1 or 2 amino groups, 1 or 2 nitro groups, 1 or 2 cyano groups, 1 or 2 thiol groups, and/or 1 or 2 -alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy" or "aralkoxy" as employed herein alone or as part of another group includes any of the above lower alkyl, alkyl or aralkyl groups linked to an oxygen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl,3-nonynyl, 4-decynyl, 3-undecynyl, 4-dodecynyl and the like.

The terms $(CH_2)_m$, $(CH_2)_n$ and $(CH_2)_p$ includes straight or branched chain radicals having from 0 to 4 carbons in the normal chain in the case of $(CH_2)_m$, from 1 to 5 carbons in the normal chain in the case of $(CH_2)_n$ and from 1 to 4 carbons in the normal chain in the case of $(CH_2)_p$ and may contain one or more lower alkyl and/or halogen substituents. Examples of $(CH_2)_m$, $(CH_2)_n$ and $(CH_2)_p$ groups include

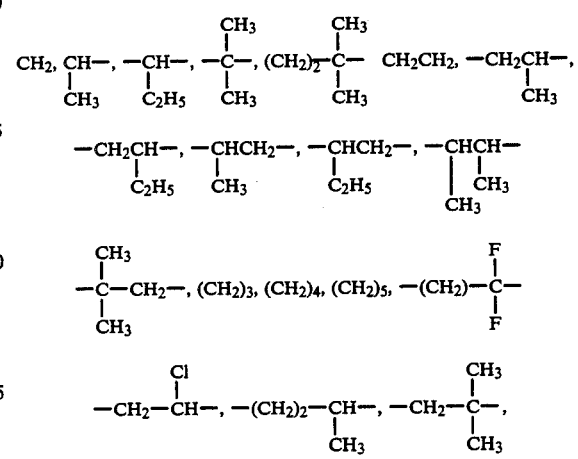

-continued

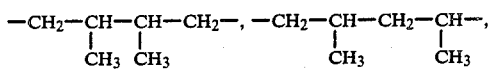

and the like.

The term $(CH_2)_q$ includes straight or branched chain radicals having from 1 to 12 carbons in the normal chain and includes any of the above examples of $(CH_2)_m$, $(CH_2)_n$ and $(CH_2)_p$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, thiol, alkylthio, arylthio, cyano or nitro groups.

The term "polyhydroxyamine salt" refers to glucamine salt or tris(hydroxymethyl)aminomethane salt.

The term "halogen" or "halo" as used herein refers to chlorine, bromine, fluorine, iodine and $CF_3$, with chlorine or fluorine being preferred.

Preferred are those compounds of formula I wherein m is 1, A is a —CH=CH—, n is 1 to 4, R is $CO_2H$; p is 1, $R^1$ is H, $(CH_2)_q$ is —$CH_2$— or —$CH_2$—$CH_2$—; $R^2$ is H or $CH_3$, and $R^3$ is lower alkyl, such as butyl, pentyl, hexyl, or heptyl or aryl, such as phenyl or p-methoxyphenyl.

The compounds of formula I of the invention may be prepared as described below.

A. p is 1, m is 1, and $R^1$ is H

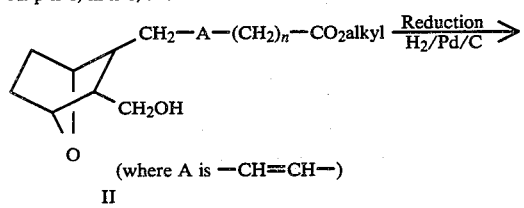

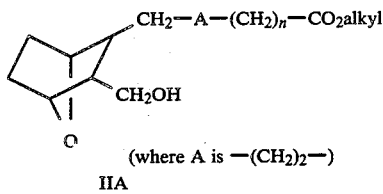

II or IIA $\xrightarrow{\text{Tosylation}}_{\text{TsCl/pyridine}}$

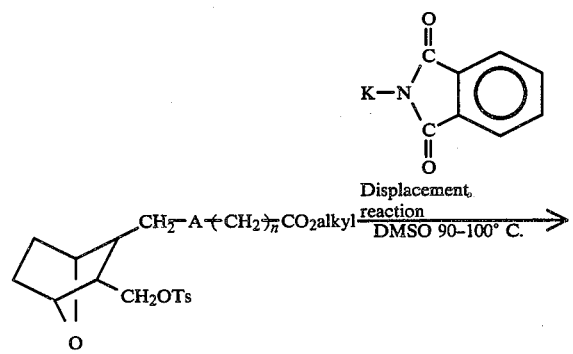

-continued

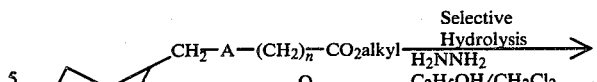

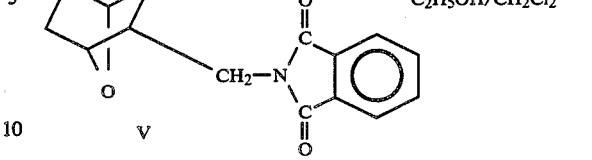

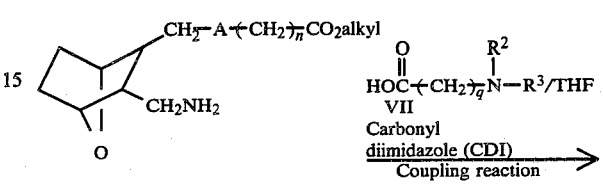

A'. Where p is 1, m is 1, and $R^1$ is alkyl

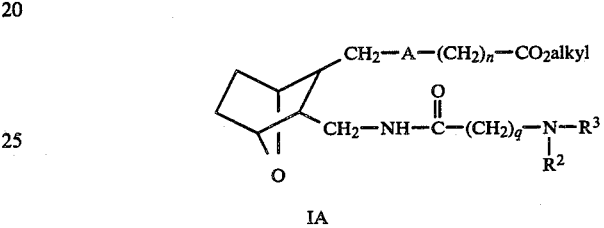

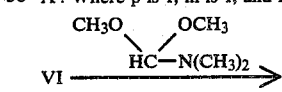

VI'

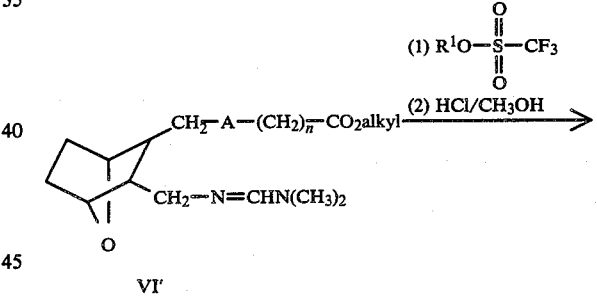

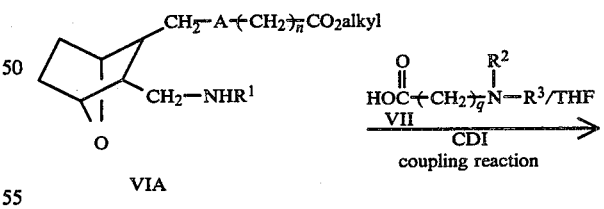

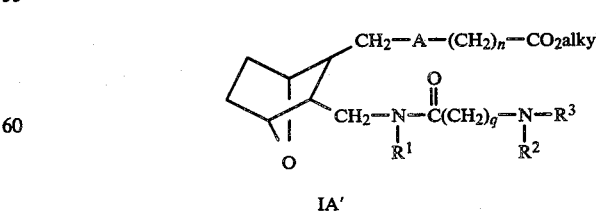

B. Where p is 2 to 4, m is 1 and $R^1$ is H

II or IIA $\xrightarrow{\text{Collins oxidation}}$ 4,656,185
-continued
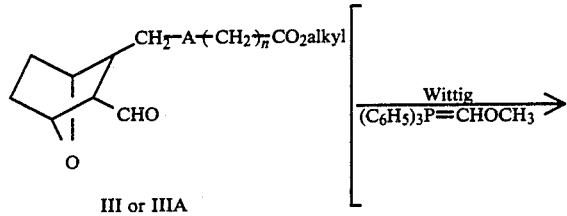
III or IIIA
III (where A is —CH=CH—)
IIIA (where A is —(CH₂)₂—)
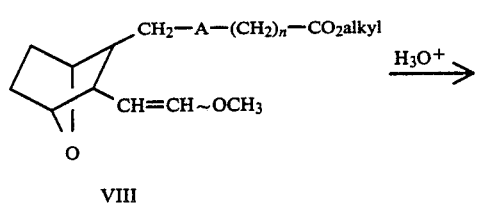
VIII
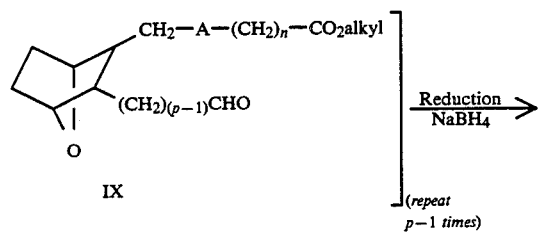
IX
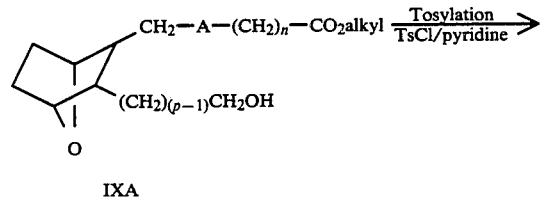
IXA
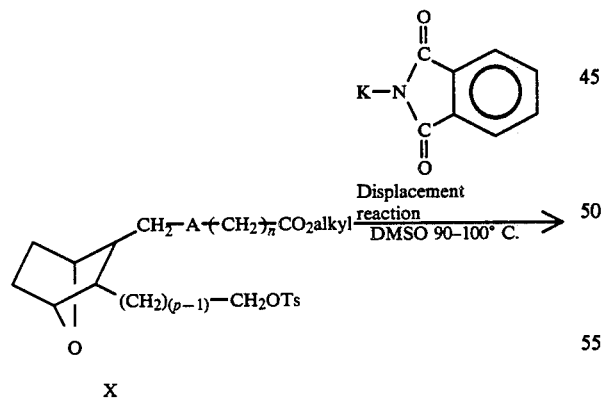
X
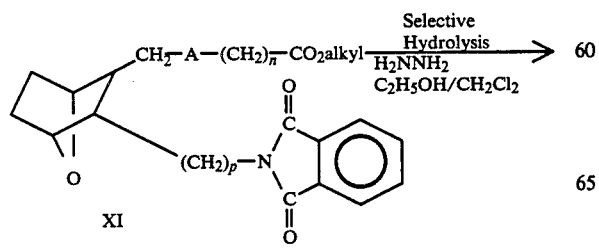
XI
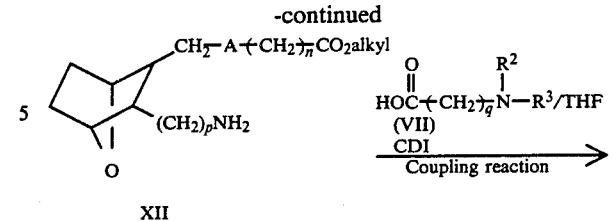
XII
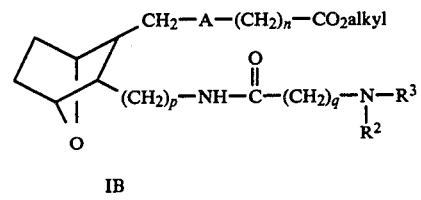
IB
B'. Where p is 2 to 4, m is 1 and $R^1$ is alkyl
XII $\xrightarrow[\text{dimethylacetal)}]{\text{(1) } CH_3O\,\,HC\,\,OCH_3 \;\; N(CH_3)_2 \atop \text{(N,N—dimethylformamide}}$
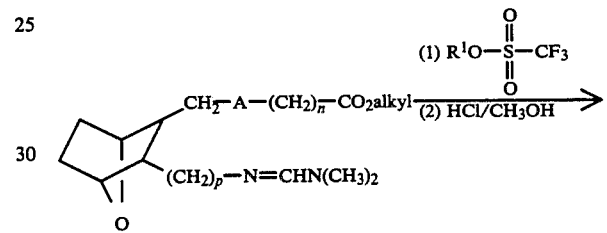
XII'
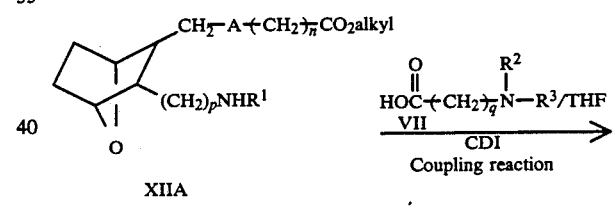
XIIA
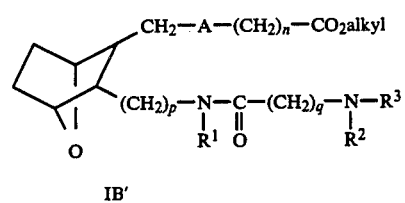
IB'
C. Where m is 2, p is 1, and A is —CH=CH—
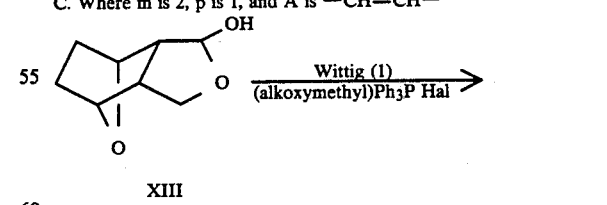
XIII
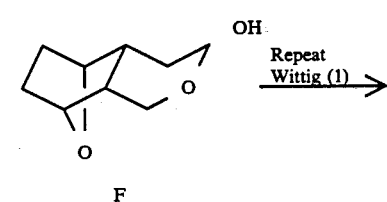
F -continued
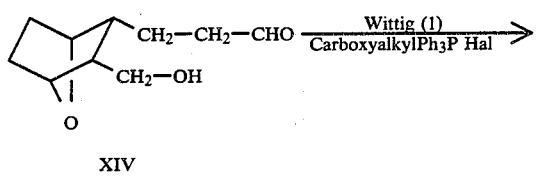
XIV
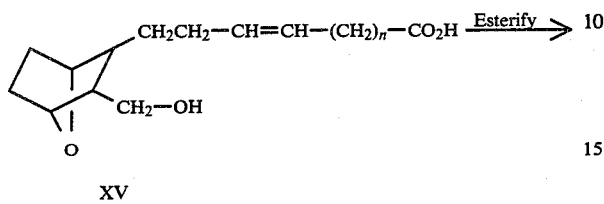
XV
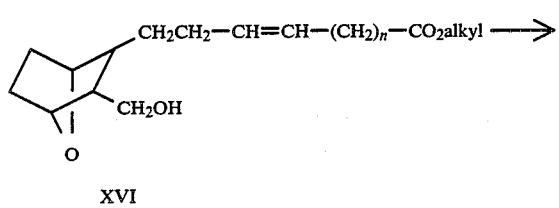
XVI
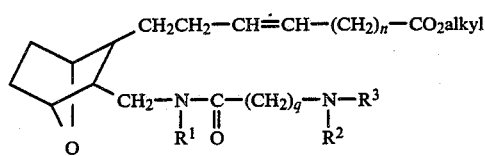
IC
D. m is 2, p is 1, and A is —CH₂—CH₂—
XVI $\xrightarrow{\text{Reduction}}_{\text{H}_2/\text{Pd/C}}$
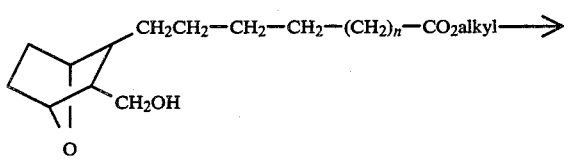
XVIA
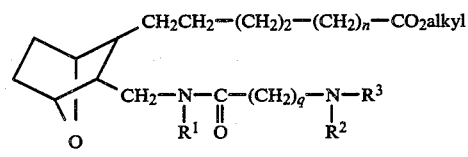
ID
E. Where m is 3 or 4, p is 1, A is —CH=CH—
Repeat Wittig (1)
1 time if m is 3
and 2 times if
XIV $\xrightarrow{\text{m is 4}}$
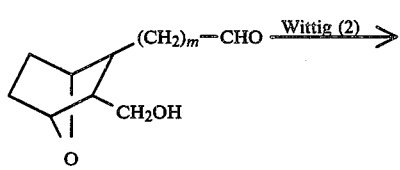
XVII
-continued
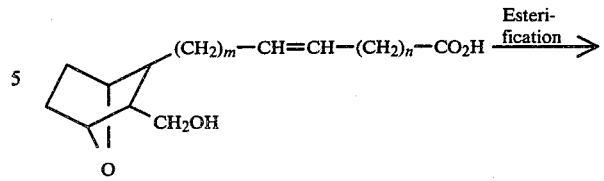
XVIII
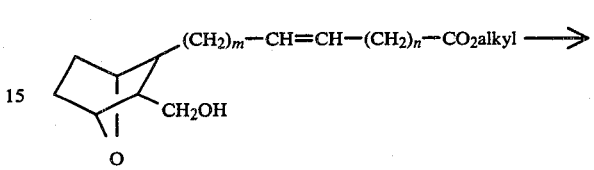
XIX
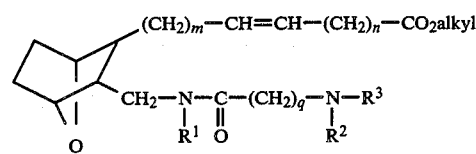
IE
F. Where m is 3 or 4, p is 1, and A is CH₂CH₂
XIX $\xrightarrow{\text{Reduction}}_{\text{H}_2/\text{Pd/C}}$
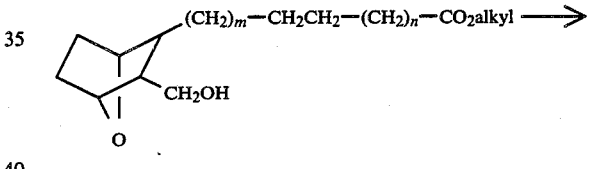
XIXA
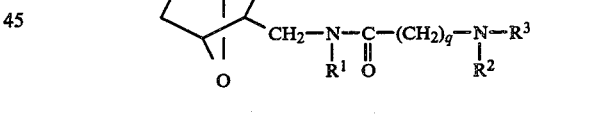
IF
F. Where m = 0, A is —CH=CH—, p is 1
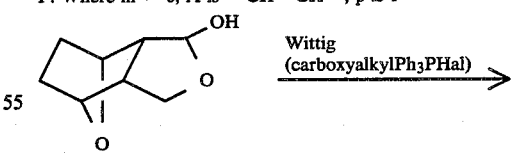
XIII
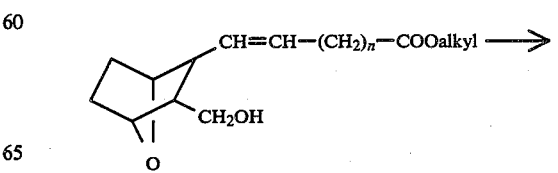
IXB -continued

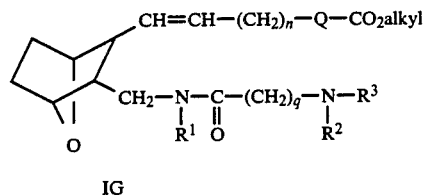
IG

H. Where m = 0, A is —(CH$_2$)$_2$—, p is 1

IXB $\xrightarrow[\text{H}_2/\text{Pd/C}]{\text{Reduction}}$

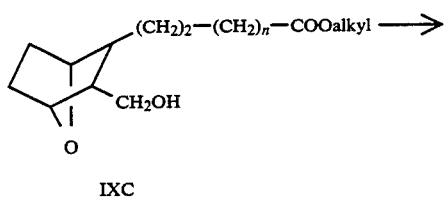
IXC

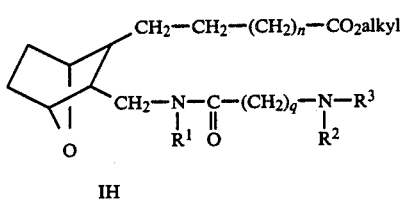
IH

I. Where R is $\overset{\overset{O}{\|}}{C}$NR$^4$R$^5$ (wherein R$^4$ and R$^5$ are other than hydroxy or alkoxy)

IA, IA', IB, IB', IC, ID, IE, IF, IG, IH $\xrightarrow{\text{HNR}^4\text{R}^5}$

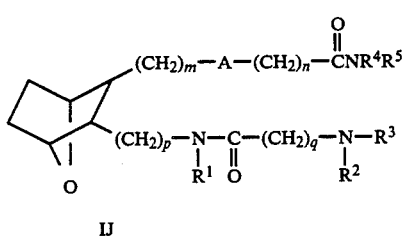
IJ

J. Where R is  and A is CH=CH

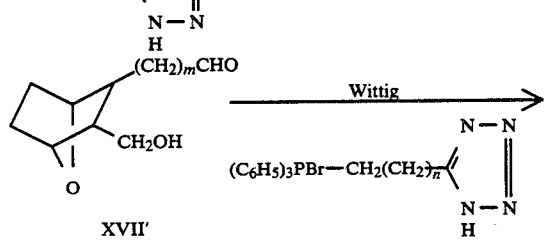

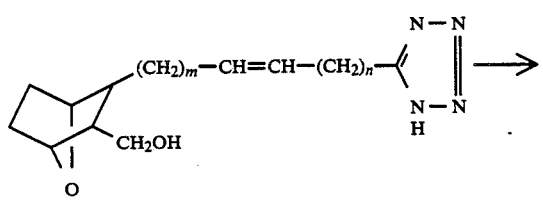
IIC

-continued

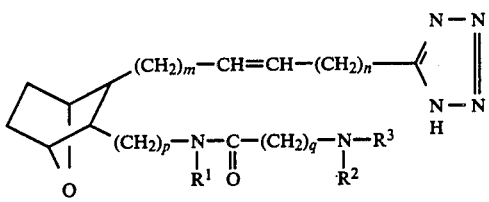
IK

K. Where R is 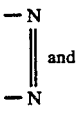 and A is (CH$_2$)$_2$

IK $\xrightarrow[\text{H}_2/\text{Pd/C}]{\text{Reduction}}$

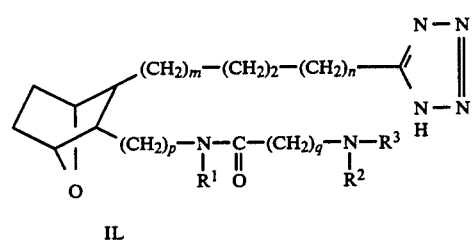
IL

L. Where R is CH$_2$OH

IA to IH $\xrightarrow[\text{LiBH}_4]{\text{NaBH}_4 \text{ or}}$

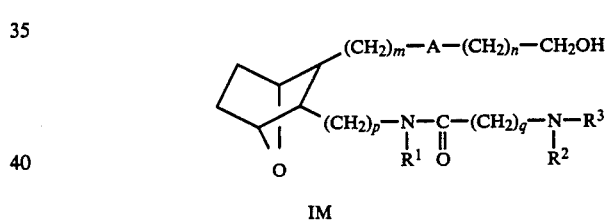
IM

M. Where R is CO$_2$H

IA to IH $\xrightarrow[\text{LiOH, HCl}]{\text{Hydrolysis}}$

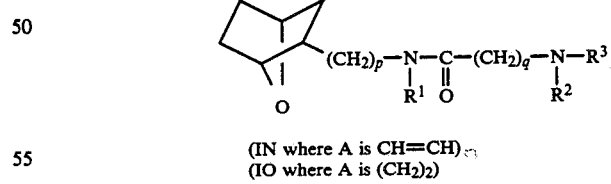

(IN where A is CH=CH)
(IO where A is (CH$_2$)$_2$)

N. Where R is $\overset{\overset{O}{\|}}{C}$N—OR$^{5'}$
             $\underset{R^4}{|}$ IN or IO $\xrightarrow[\text{(2) HN}\overset{OR^{5'}}{\underset{R^4}{\diagdown}} \cdot \text{HCl/(C}_2\text{H}_5)_3\text{N}]{\text{Hydroxamate Formation} \atop \text{(1) Carbonyldiimidazole (CDI)}}$ (wherein R$^{5'}$ is H or alkyl)

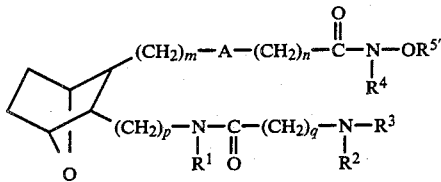

IP

As seen in reaction sequence "A", compounds of the invention where p is 1, R is CO$_2$alkyl, and R$^1$ is H, that is

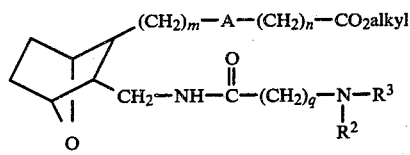

IA are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

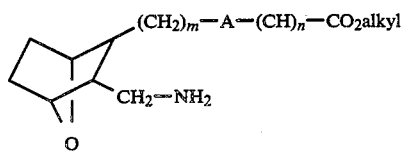

VI

As seen in reaction sequence "A'", where R$^1$ is lower alkyl, an alkylation reaction is carried out as in the reference M. J. O'Donnell et al., *Tetrahedron Lett.* (1984), 25, 3651-3654 to give VIA

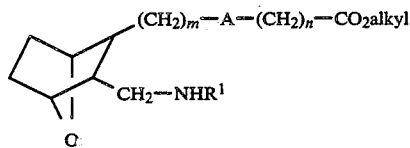

VIA

The amine VI or VIA is then subjected to a CDI coupling reaction by reacting VI or VIA with acid VII

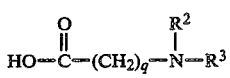

VII in the presence of an inert organic solvent such as tetrahydrofuran and carbonyl diimidazole under an inert atmosphere, such as argon, employing a molar ratio of VI:VIII of within the range of from about 1:1 to about 1:1.2, to form the amide ester compound of the invention IA or IA'

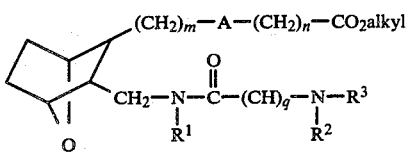

(IA—where R$^1$ is H, IA'—where R$^1$ is lower alkyl).

The reaction sequences identified as "B" and "B'" are employed to prepare compounds of the invention wherein p is 2 to 5, and R is CO$_2$alkyl, that is,

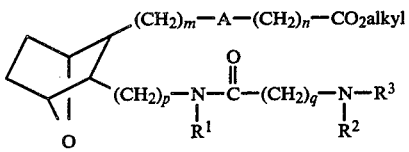

(where p is 2 to 4)

(IB—where R$^1$ is H, IB'—where R$^1$ is alkyl).

Compound II or IIA is used to form the aldehyde III (where A is —CH=CH—) or IIIA (where A is —(CH$_2$)$_2$). Thus, to form aldehyde III where A is —CH=CH—, compound II is subjected to a Collins oxidation, for example, by reacting II with chromium trioxide in pyridine. To form the aldehyde IIIA (where A is (CH$_2$)$_2$) compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$). The aldehyde III or IIIA is used to prepare aldehyde IX (where p is 2–4) by carrying out a homologation sequence, such as a Wittig reaction with (C$_6$H$_5$)$_3$P=CHOMe followed by hydrolysis, (p-1) times. The aldehyde IX (where p is 2–4) is then carried on to compounds of this invention where p is 2-4, that is

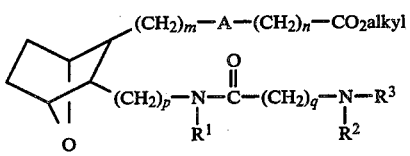

IB (where p is 2 to 4).

by reducing aldehyde IX by reacting with a reducing agent such as sodium borohydride to form alcohol IXA

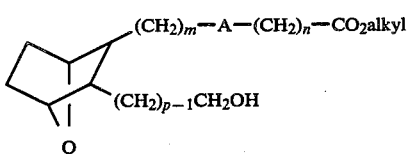

IXA tosylating alcohol IXA as described above to form the tosylate X which is subjected to a displacement reaction with potassium phthalimide as described above to form the phthalimide XI. Phthalimide XI is then made to undergo selective hydrolysis as described above to form the amine XII

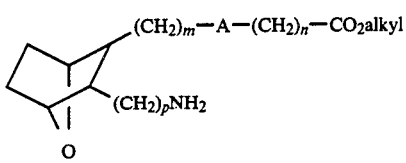

As seen in reaction sequence "B'", where $R^1$ is lower alkyl, an alkylation reaction is carried out as in O'Donnell et al, supra to give XIIA

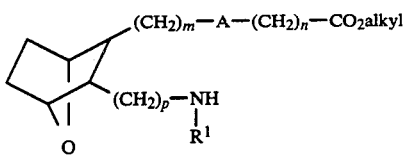

The amine XII or XIIA is then reacted with acid VII in a CDI coupling reaction as described above to form the amide ester compound of the invention IB or IB'

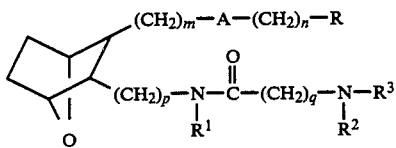

(IB—where $R^1$ is H, IB'—where $R^1$ is lower alkyl).

Compounds of the invention wherein m is 2, A is —CH=CH— and p is 1 may be prepared as outlined in reaction sequence "C" by subjecting starting compound XIII to a Wittig reaction, referred to as Wittig (1), by reacting XIII with an alkoxymethyltriphenyl phosphonium halide, such as (methoxymethyl)triphenylphosphonium chloride, for example, as described in Example 4 of U.S. Pat. No. 4,143,054, to form compound F. The Wittig (1) procedure is repeated on compound F to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is then employed in place of compound II in reaction scheme "A" to form compound IC of the invention.

As seen in reaction sequence "D", compounds of the invention wherein m is 2, A is —CH$_2$—CH$_2$—, and p is 1 may be prepared as outlined in reaction sequence "D" by reducing hydroxymethyl compound XVI to form compound XVIA which is then employed in place of compound IIA in reaction sequence "A" to form compound ID of the invention.

Referring to reaction sequence "E", compounds of the invention wherein m is 3 or 4, A is —CH=CH—, and p is 1 may be prepared by subjecting aldehyde XIV to the Wittig (1) procedure one time in the case where m is 3 and a second time in the case where m is 4, to form the aldehyde XVII. Aldehyde XVII is then subjected to the Wittig (2) procedure to form acid XVIII which is esterified to form ester XIX which is then employed in place of compound II in reaction scheme "A" to form compound IE of the invention.

As seen in reaction sequence "F", compounds of the invention wherein m is 3 or 4, A is CH$_2$CH$_2$, and p is 1 may be prepared by reducing hydroxymethyl compound XIX to form compound XIXA which is then employed in place of compound II in reaction scheme "A" to form compound IF of the invention.

Thus, compounds of the invention wherein m is 0, 2, 3 or 4 and p is 2, 3 or 4 may be prepared by substituting hydroxymethyl compound XVI, XVIA, XIX, or XIXA in place of hydroxymethyl compound II or IIA in reaction sequences A and B.

Referring now to reaction sequence "G", compounds of the invention wherein m is 0, A is CH=CH, and p is 1, that is, compound IG may be prepared by subjecting compound XIII (prepared as described in Example 3 of U.S. Pat. No. 4,143,054) to a Wittig reaction, for example, as described in Example 6(c) of U.S. Pat. No. 4,143,054, by reacting XIII with a carboxyalkyltriphenyl phosphonium halide, such as carboxypentyltriphenyl phosphonium bromide to form the hydroxymethyl compound IXB which may then be used to form the ester IG which, in turn, may be hydrolyzed to the corresponding acid.

As seen in reaction sequence "H", where it is desired to prepare compounds of the invention wherein m is 0 and A is (CH$_2$)$_2$, the hydroxymethyl compound IXB is reduced by treatment with hydrogen in the presence of a palladium on carbon catalyst to form hydroxymethyl compound IXC which may then be used to form ester IH which then may be hydrolyzed to the corresponding acid.

In reaction sequence "I", amides of the invention of structure IJ

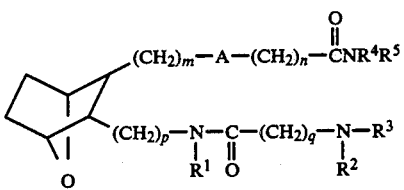

wherein $R^4$ and $R^5$ are independently H, alkyl or aryl are prepared by treating ester IA to IH with an amine of the structure

HNR$^4$R$^5$.     E

Compounds of the invention wherein R is tetrazole

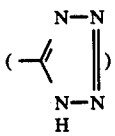

and A is CH=CH are prepared as described in reaction sequence "J" wherein alcohol XVII

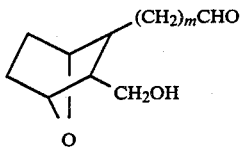                                    XVII (prepared as described in U.S. Pat. No. 4,143,054) is reacted with a Wittig reagent of the structure G

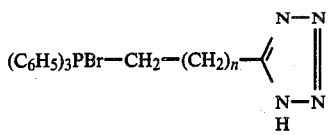   G in the presence of a base, such as potassium t-butoxide or sodium hydride-dimethyl sulfoxide employing a molar ratio of XVII:G of within the range of from about 1:1 to about 0.2:1 to form the hydroxymethyl compound IIC

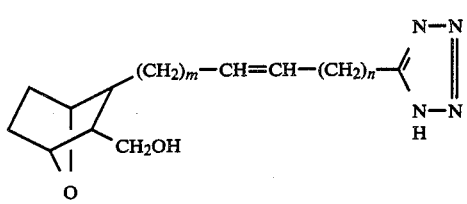   IIC which may then be employed in reaction sequences "A" and "B" in place of compounds II or IIA to form compounds of the invention IK where A is —CH=CH— or IL where A is $(CH_2)_2$

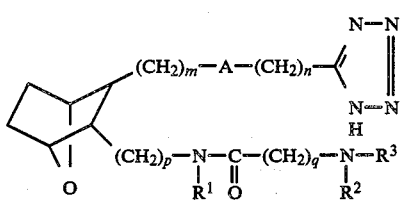   IK or IL

Alternatively, compound IL may be prepared by reducing compound IK by treating with $H_2$ in the presence of palladium on charcoal.

As seen in reaction sequence "L", compounds of the invention wherein R is $CH_2OH$ may be prepared by reducing esters IA to IH, by treatment with sodium borohydride or lithium borohydride to form compounds of the invention IM

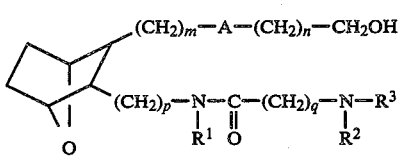   IM

Referring to reaction sequence "M", the esters IA, IA', IB, IB' to IH can be converted to the free acid, that is, to

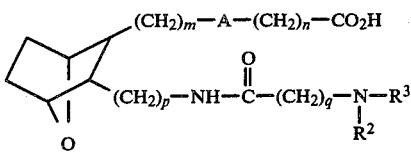

IN (A is —CH=CH—), IO (A is $(CH_2)_2$).

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IN and IO.

In the reaction sequence identified as "N" where in Formula I, R is

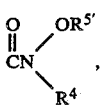

wherein $R^{5'}$ is H or alkyl, a solution of acid dissolved in an inert organic solvent such as tetrahydrofuran (THF) is treated with carbonyldiimidazole (CDI) and the mixture is stirred at room temperature under nitrogen. The resulting active ester is dissolved in an inert organic solvent such as tetrahydrofuran and the so-formed solution is added dropwise into a cold solution of amine hydrochloride H

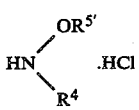   H (wherein $R^{5'}$ is H or alkyl, employing a molar ratio of acid chloride:H of within the range of from about 0.3:1 to about 1:1 and preferably from about 0.5:1) and triethylamine in tetrahydrofuran to form the hydroxamate IP.

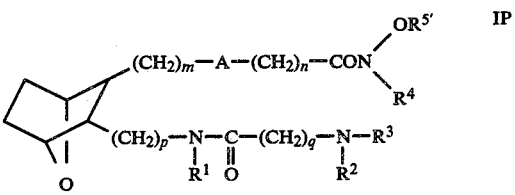   IP

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

The starting acid VII

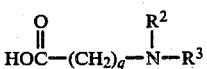   VII may be prepared by reacting the amine J

   J with a halo ester K employing a molar ratio of about 1:1 to 1:1.5 (ester:amine) in a solvent such as ethyl alcohol and in the presence of excess tertiary amine such as triethylamine to form ester K'

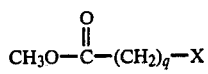   K

X = Cl, Br, I

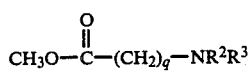   K' which may be hydrolyzed to the corresponding acid K"

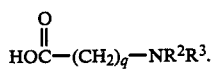   K"

Where in the starting acid VII one of $R^2$ and $R^3$ is H, it may be desired, on an optional basis, to replace the H in acid VII with a protecting group such as a tetrahydropyranyl, t-butyldimethylsilyl, ethoxyethyl or butoxycarbonyl (BOC) employing conventional procedures to form the protected acid VIIA

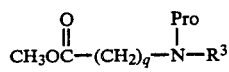   VIIA (wherein Pro represents the protecting group).

Acid VIIA may be used in place of acid VII in the reaction sequences described above to form the ester IQ

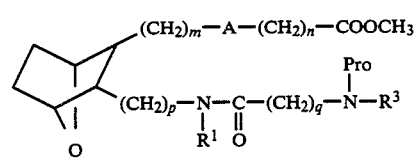   IQ which is hydrolyzed to the corresponding acid IR

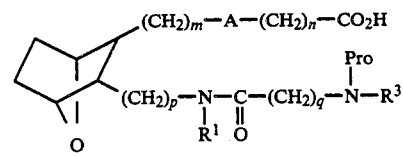   IR

The protecting group is removed by treating the acid IR with trifluoroacetic acid or other acid such as p-toluenesulfonic acid or dilute aqueous HCl.

As indicated, the compounds of the invention may be in the form of their physiologically or pharmaceutically acceptable acid-addition salts.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic acid, theophylline, 8-chlorotheophylline, p-aminobenzoic, p-acetamidobenzoic, or methanesulfonic.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

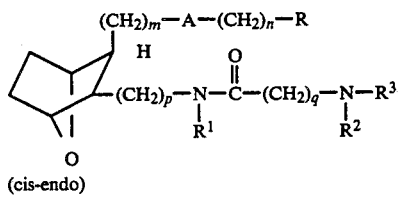   Ia (cis-endo)

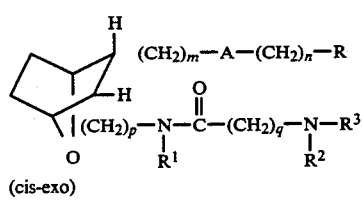   Ib (cis-exo)

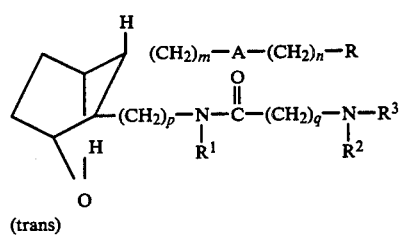   Ic (trans)

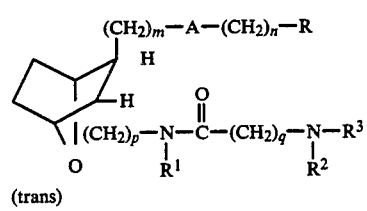   Id (trans)

The nucleus in each of the compounds of the invention is depicted as

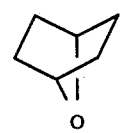

for matter of convenience; it will also be appreciated that the nucleus in the compounds of the invention may be depicted as

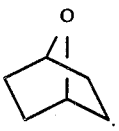

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 0.1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1β,2α(5Z),3α,4β]]-7-[3-[[[(Hexylamino)acetyl]amino]methyl]-7-oxabicyclo[2.2.1]hept-2-yl]-5-heptenoic acid A. N-(t-butoxycarbonyl)-N-hexyl glycine (1) N-Hexylglycine methyl ester A solution of 5.0 ml (37.9 mmol) of hexylamine and 6.0 ml (43.1 mmol) of triethylamine in 25 ml of absolute ethanol was cooled in an ice-bath. To the stirred solution was added dropwise 3.6 ml (38.0 mmol) of methyl bromoacetate. The ice-bath was removed. The flask warmed to ~30° C. so the flask was placed in a cold water (~15° C.) bath. After stirring for 4 hours, the reaction mixture was concentrated to ~5-10 ml and diluted with 100 ml of ether. The white precipitate which formed was filtered off and the filtrate concentrated in vacuo. Chromatography on 80 g of silica gel using 2% MeOH/CH$_2$Cl$_2$ as eluant afforded 2.0 g of title A (1) amine.

(2) N-(t-Butoxycarbonyl)-N-hexyl glycine, methyl ester

To a solution of 2.0 g Part A (1) amine in 20 ml of CH$_2$Cl$_2$ was added 3.8 g (17.4 mmol) of di-t-butyldicarbonate. This solution was stirred overnight at room temperature, concentrated in vacuo and chromatographed on 95 g of silica gel using 4:1 hexane-ether as eluant to afford 1.8 g title A (2) ester.

(3) N-(t-Butoxycarbonyl)-N-hexyl glycine

To a stirred solution of 1.8 g Part A (2) ester in 40 ml of tetrahydrofuran and 7.5 ml of H$_2$O was added 15 ml of 1N LiOH solution. After stirring for 3 hours, the reaction mixture was partitioned between 50 ml each EtOAc and saturated NaCl solution. The aqueous layer was acidified to pH ~3 and extracted with two 50 ml portions of EtOAc. The combined EtOAc layers were dried over MgSO$_4$, filtered and concentrated in vacuo to afford 1.7 g of title acid.

B. [1S-[1β,2α(5Z),3α,4β]]-7-[3-(Tosyloxymethyl)-7-oxabicyclo[2.2.1]hept-2-yl]-5-heptenoic acid, methyl ester Tosyl chloride (4.256 g, 22.4 mmol) dissolved in CH$_2$Cl$_2$ (30 ml) was added dropwise to a magnetically stirred solution of [1S-[1β,2α(5Z),3α,4β]]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/H$_2$O and stirred for 30 minutes. The products were extracted with EtOAc (80 ml×3). The combined EtOAc layers were washed with 3N-HCl (40 ml×3), saturated NaHCO$_3$, brine and dried over MgSO$_4$. Filtration and evaporation of solvent gave a white solid, which was crystallized from isopropyl ether to give the corresponding title tosylate in the form of needle crystals (4.23 g, 89%), m.p. 68°-70° C.

C. [1S-[1β,2α(5Z),3α,4β]]-7-[3-(Aminomethyl)-7-oxabicyclo[2.2.1]hept-2-yl]-5-heptenoic acid, methyl ester The title B tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title B tosylate (8.11 g, 19.2 mmol) and purified potassium phthalimide (6.4 g, 34.6 mmol, 1.8 equiv.) in dimethylsulfoxide (70 ml, Burdick & Jackson) were heated at 90°-100° C. for 2½ hours (checked by TLC Et$_2$O-pet ether 2:1, no tosylate remaining). After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3×50 ml), dried (MgSO$_4$), filtered and freed of solvent in vacuo. The remaining solid (7.88 g) was recrystallized from isopropyl ether (~150 ml) to give corresponding phthalimide (6.35 g, 83%) TLC. Et$_2$O-hexane 2:1, UV+vanillin R$_f$=0.38, trace 0.09.

The above phthalimide (5.05 g, 13.8 mmol) was dissolved in distilled CH$_2$Cl$_2$ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more $CH_2Cl_2$. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid $K_2CO_3$. The amine was extracted into $CHCl_3$ (3×100 ml), dried ($MgSO_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

D.
[1S-[1β,2α(5Z),3α,4β]]-7-[3-[[[[N-(t-Butoxycarbonyl)-hexylamino]acetyl]amino]methyl]-7-oxabicyclo[2.2.1-]hept-2-yl]-5-heptenoic acid, methyl ester A solution of 378 g (1.46 mmol) of Part A acid in 5.0 ml of THF was cooled in an ice-bath under Ar. To this stirred solution was added 245 mg (1.51 mmol) of 1,1'-carbonyl diimidazole. After stirring at 0° C. for 15 minutes, the reaction mixture was allowed to warm to room temperature. Five minutes later a solution of 320 mg (1.2 mmol) of Part C amine in 3.0 ml of THF was added. The resulting solution was stirred for 20 hours at room temperature, and then partitioned between 50 ml each of 1N HCl and EtOAc. The aqueous layer was extracted with 50 ml EtOAc. The combined EtOAc layers were washed with 30 ml of $H_2O$, dried over $MgSO_4$, filtered and concentrated in vacuo. Purification was effected by flash chromatography on 35 g of silica gel using 2% $MeOH/CH_2Cl_2$ as eluant to afford 320 mg (52%) of title ester.

E.
[1S-[1β,2α(5Z),3α,4β]]-7-[3-[[[[N-(t-Butoxycarbonyl)-hexylamino]acetyl]amino]methyl]-7-oxabicyclo[2.2.1-]hept-2-yl]-5-heptenoic acid To a stirred solution of 320 mg (0.63 mmol) of Part D ester in 10 ml of THF was added 1.0 ml $H_2O$ and 2.0 ml of 1N LiOH solution. After stirring at room temperature for 6 hours, the reaction mixture was poured into 25 ml saturated NaCl solution. The pH was adjusted to ~2 and the combined EtOAc layers were dried over $Na_2SO_4$, filtered and concentrated in vacuo. Flash chromatography on 25 g of silica gel using 3% $MeOH/CH_2Cl_2$ as eluant afforded 270 mg (87%) of title acid.

F.
[1S-[1β,2α(5Z),3α,4β]]-7-[3-[[[(Hexylamino)acetyl]amino]methyl]-7-oxabicyclo[2.2.1]hept-2-yl]-5-heptenoic acid To a flask containing 270 mg (0.55 mmol) of Part E acid at 0° C. was added 3.0 ml of pre-cooled (0° C.) trifluoroacetic acid. The resulting solution was stirred at 0° C. for 1 hour and then the trifluoroacetic acid was removed in vacuo. Flash chromatography on 22 g of silica gel using 4% $CH_3OH/CH_2Cl_2$ as eluant afforded 180 mg of slightly impure title and 60 mg of the corresponding methyl ester. The latter was hydrolyzed by treatment with 0.5 ml of 1N LiOH in a solution of 0.5 ml $H_2O$ and 3.0 ml THF. After stirring for 7 hours, the reaction mixture was partitioned between 10 ml each of saturated KCl and EtOAc. The acidified aqueous layer (pH 4.5) was extracted with two 25 ml portions of $CHCl_3$. The combined organic layers were dried over $MgSO_4$, filtered and concentrated in vacuo.

EXAMPLE 2
[1S-[1β,2α(5Z),3α,4β]]-7-[3-[[[(Hexylamino)acetyl]amino]methyl]-7-oxabicyclo[2.2.1]hept-2-yl]-5-heptenoic acid, monohydrochloride The HCl salt was prepared by adding several drops of concentrated HCl to a THF solution of the Example 1 acid. The residue was triturated with ether. Collection of solid gave 78 mg of the title HCl-salt, m.p. 63°–66° C. $[\alpha] = -5.5°$ (c=1.34, MeOH).

TLC: silica gel, 10% $CH_3OH/CH_2Cl_2$, $R_f$=0.60 Ce($SO_4)_2$.

Anal Calcd for $C_{22}H_{38}N_2O_4 \cdot HCl$: C, 58.85; H, 9.20; N, 6.24; Cl, 7.90. Found: C, 58.95; H, 8.86; N, 6.40; Cl, 7.88.

EXAMPLE 3
[1S-[1β,2α(5Z),3α,4β]]-7-[3-[[[[(4-Methoxyphenyl)amino]acetyl]amino]-7-oxabicyclo[2.2.1]hept-2-yl]-5-heptenoic acid

A. N-(4-Methoxyphenyl)glycine

The title acid was prepared by direct alkylation of p-anisidine with bromoacetic acid in the presence of triethylamine following the procedure outlined in Example 1 Part A.

B.
[1S-[1β,2α(5Z),3α,4β]]-7-[3-[[[[(4-Methoxyphenyl)amino]acetyl]amino]-7-oxabicyclo[2.2.1]hept-2-yl]-5-heptenoic acid, methyl ester A solution of 460 mg (2.7 mmol) of Part A acid in 8 ml of THF and 1 ml of DMSO was cooled to 0° C. To this solution was added 460 mg (2.84 mmol) of 1,1'-carbonyldiimidazole. After stirring at 0° C. for 75 minutes, the reaction mixture was allowed to warm to room temperature. After an additional 90 minutes, a solution of 480 mg (1.8 mmol) of Example 1 Part C amine in 5 ml of THF was added. The resultant solution was allowed to stir at room temperature for 20 hours. The reaction mixture was then partitioned between 50 ml each of half-saturated NaCl solution and ethyl acetate. The aqueous layer was acidified to pH=5 with 1N HCl, then shook with the EtOAc layer and reacidified until pH=5. The aqueous layer was extracted with 50 ml of additional EtOAc. The combined EtOAc layers were washed with 25 ml of water, dried over $MgSO_4$, filtered and concentrated in vacuo. The crude product was chromatographed on 40 g of silica gel using 4% $CH_3OH/CH_2Cl_2$ as eluant. This afforded 360 mg (46%) of title ester.

TLC: silica gel; 4% $CH_3OH/CH_2Cl_2$, $R_f$=0.5, Ce($SO_4)_2$.

C.
[1S-[1β,2α(5Z),3α,4β]]-7-[3-[[[[(4-Methoxyphenyl)amino]acetyl]amino]-7-oxabicyclo[2.2.1]hept-2-yl]-5-heptenoic acid To a stirred solution of 350 mg (0.81 mmol) of Part B ester in 10.0 ml of THF and 1.0 ml of $H_2O$ was added 2.0 ml of 1N LiOH solution. TLC analysis after 7 hours showed the reaction to be complete. The reaction mixture was partitioned between 10 ml each of saturated KCl solution and EtOAc. The aqueous layer was acidified to pH 4.5-5.0 and extracted with the EtOAc layer. This process was repeated until pH was constant. The aqueous layer was then extracted with two 25 ml portions of $CHCl_3$. The combined organic layers were dried over $MgSO_4$, filtered and concentrated in vacuo. Purification was affected by silica gel (22 g) chromatography using 4% $CH_3OH/CH_2Cl_2$ as eluant.

EXAMPLE 4
[1S-[1β,2α(5Z),3α,4β]]-7-[3-[[[[(4-Methoxyphenyl)amino]acetyl]amino]-7-oxabicyclo[2.2.1]hept-2-yl]-5-heptenoic acid, monohydrochloride The Example 3 product was dissolved in minimal THF and several drops of concentrated HCl were added. The solution was concentrated in vacuo. The residue was dissolved in ether/toluene and concentrated in vacuo. The resulting solid was dissolved in ~1 ml of warm isopropyl alcohol and 3 ml of ether was added. After standing at room temperature, the flask was chilled. The off-white solid was collected and dried in vacuo to afford 110 mg (30%) of the hydrochloride of the Example 3 amino-acid, m.p. 126°-128° (dec.); $[\alpha]^D = -5.4°$ (C=0.93, $CH_3OH$).

TLC of acid HCl, silica gel, 10% $MeOH/CH_2Cl_2$, $R_f = 0.4$ $Ce(SO_4)$

Anal Calcd for $C_{23}H_{32}N_2O_5 \cdot HCl$: C, 60.98; H, 7.34; N, 6.19; Cl, 7.83. Found: C, 60.86; H, 7.31; N, 6.25; Cl, 7.94.

EXAMPLE 5
[1S-[1β,2α(5Z),3α,4β]]-N-Methyl-7-[3-[[[Hexylamino)acetyl]amino]methyl]-7-oxabicyclo[2.2.1]hept-2-yl]-5-heptenamide 40% $MeNH_2$ in $H_2O$ (2 ml) is added to a magnetically stirred solution of ester prepared in Example 1 (153 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 6
[1S-(1β,2α,3α,4β)]-7-[3-[[[(Hexylamino)acetyl]amino]methyl]-7-oxabicyclo[2.2.1]hept-2-yl]heptanoic acid, methyl ester

A.
[1S-(1β,2α,3α,4β)]-7-[3-(Hydroxymethyl)-7-oxabicyclo[2.2.1]hept-2-yl]heptanoic acid, methyl ester To 800 mg (3.0 mmole) of the [1S-[1β,2α(Z),3α,4β]]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.
[1S-(1β,2α,3α,4β)]-7-[3-[[[(Hexylamino)acetyl]amino]methyl]-7-oxabicyclo[2.2.1]hept-2-yl]heptanoic acid, methyl ester Following the procedure of Example 1 except substituting the Part A alcohol-ester for the alcohol ester employing in Example 1 Part B, the title product is obtained.

EXAMPLE 7
[1S-[1β,2α(5Z),3α,4β]]-7-[3-[[[(4-Biphenylamino)acetyl]amino]methyl]-7-oxabicyclo[2.2.1]hept-2-yl]-5-heptenoic acid, methyl ester

A. N-(4-Biphenylamino)glycine

Following the procedure of Example 2 except substituting 4-aminobiphenyl for p-anisidine the title compound is obtained.

B.
[1S-[1β,2α(5Z),3α,4β]]-7-[3-[[[4-Biphenylamino]acetyl]amino]methyl]-7-oxabicyclo[2.2.1]hept-2-yl]-5-heptenoic acid methyl ester Part A acid (1 mmol) is reacted with carbonyldiimidazole (1 mmole) followed by [1S-[1β,2α(5Z),3α,4β]]-7-[3-(aminomethyl)-7-oxabicyclo[2.2.1]hept-2-yl]-5-heptenoic acid, methyl ester (1 mmole) as prepared in Example 1, Part C. After stirring overnight at room temperature, DMF (3 ml) is added to give a nearly clear reaction mixture and the mixture is left stirring an additional 24 hours. After the usual work up, the viscous product is chromatographed on silica gel (30 g of Baker for flash chromatography), eluting with 2% MeOH in $CH_2Cl_2$ to give title ester.

EXAMPLE 8
[1S-[1β,2α(5Z),3α,4β]]-7-[3-[[[(4-Biphenylamino)acetyl]amino]methyl]-7-oxabicyclo[2.2.1]hept-2-yl]-5-heptenoic acid The Example 7 methyl ester is hydrolyzed with LiOH as described in Example 2 to give title acid.

EXAMPLE 9
[1S-[1β,2α(5Z),3α,4β]]-7-[3-[[(Amino)acetyl]amino]methyl]-7-oxabicyclo[2.2.1]hept-2-yl]-5-heptenoic acid Following the procedure of Examples 1 and 2 except substituting N-(t-butoxycarbonyl)glycine for Example 1 Part A acid, the title compound is obtained.

EXAMPLE 10
[1S-[1β,2α(5Z),3α,4β]]-7-[3-[[[(But-2-enylamino)acetyl]amino]methyl]-7-oxabicyclo[2.2.1]hept-2-yl]-5-heptenoic acid Following the procedure of Examples 1 and 2 except substituting 2-butenyl amine for hexylamine, the title compound is obtained.

EXAMPLE 11

[1S-[1β,2α(5Z),3α,4β]]-7-[3-[[[(But-3-ynylamino)acetyl]amino]methyl]-7-oxabicyclo[2.2.1]hept-2-yl]-5-heptenoic acid Following the procedure of Examples 1 and 2 except substituting 3-butynyl amine for hexylamine, the title compound is obtained.

EXAMPLE 12

[1S-[1β,2α(5Z),3α,4β]]-7-[3-[[[(Phenylamino)acetyl]amino]methyl]-7-oxabicyclo[2.2.1]hept-2-yl]-5-heptenoic acid Following the procedure of Examples 3 and 4 except substituting aniline for p-anisidine, the title compound is obtained.

EXAMPLE 13

[1S-[1β,2α(5Z),3α,4β]]-7-[3-[2-[[[(Hexylamino)acetyl]amino]ethyl]-7-oxabicyclo[2.2.1]hept-2-yl]-5-heptenoic acid

A.

[1S-[1β,2α(Z),3α,4β]]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride (($C_6H_5$)$_3$P$^+$—$CH_2OCH_3Cl^-$) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1S-[1β,2α(5Z),3α,4β]]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml satured NH$_4$Cl, and extracted with ether (4×200 ml). The combined ether phases were washed with NaCl, saturated solution, and dried (MgSO$_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1S-[1β,2α(Z),3α,4β]]-7-[3-(2-oxo)ethyl-7-oxabicyclo[2.2.1]hept-2-yl]-5-heptenoic acid, methyl ester, (B) [1S-[1β,2α(Z),3α,4β]]-7-[3-(2-methoxy)ethenyl-7-oxabicyclo[2.2.1]hept-2-yl]-5-heptenoic acid, methyl ester, and (C) [1S-[1β,2α(Z),3α,4β]]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1S-[1β,2α(5Z),3α,4β]]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH$_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound.

C.

[1S-[1β,2α(Z),3α,4β]]-7-[3-[2-[[[(Hexylamino)acetyl]amino]ethyl]-7-oxabicyclo[2.2.1]hept-2-yl]-5-heptenoic acid Following the procedure of Examples 1 and 2 except substituting the above part B alcohol for the alcohol used in Example 1 Part B, the title compound is obtained.

EXAMPLE 14

[1S-[1β,2α(5Z),3α,4β]]-7-[3-[4-[[[(Hexylamino)acetyl]amino]butyl]-7-oxabicyclo[2.2.1]hept-2-yl]-5-heptenoic acid

A.

[1S-[1β,2α(5Z),3α,4β]]-7-[3-(3-Oxo)propyl-7-oxabicyclo[2.2.1]hept-2-yl]-5-heptenoic acid, methyl ester Following the procedure of Example 13 Part A except substituting [1S-[1β,2α(Z),3α,4β]]-7-[3-(2-oxo)ethyl-7-oxabicyclo[2.2.1]hept-2-yl]-5-heptenoic acid, methyl ester for [1S-[1β,2α(Z),3α,4β]]-7-[3-formyl-7-oxabicyclo[2.2.1]hept-2-yl]-5-heptenoic acid, methyl ester, the title A compound is obtained.

B.

[1S-[1β,2α(Z),3α,4β]]-7-[3-(4-Oxo)butyl-7-oxabicyclo[2.2.1]hept-2-yl]-5-heptenoic acid, methyl ester Following the procedure of Example 13 Part A except substituting the aldehyde from Part A above for [1S-[1β,2α(Z),3α,4β]]-7-[3-formyl-7-oxabicyclo[2.2.1]hept-2-yl]-5-heptenoic acid, methyl ester, the title B compound is obtained.

C.

[1S-[1β,2α(Z),3α,4β]]-7-[3-(4-Hydroxybutyl)-7-oxabicyclo[2.2.1]hept-2-yl]-5-heptenoic acid, methyl ester Following the procedure of Example 13 Part B except substituting the title B aldehyde for [1S-[1β,2α(Z)-,3α,4β]]-7-[3-(2-oxo)ethyl-7-oxabicyclo[2.2.1]hept-2-yl]-5-heptenoic acid, methyl ester, the title C alcohol is obtained.

D.

[1S-[1β,2α(Z),3α,4β]]-7-[3-[4-[[[(Hexylamino)acetyl]amino]butyl]-7-oxabicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 15

1S-[1β,2α(5Z),3,α,4β]]-8-[3-[[[(Hexylamino)acetyl]amino]methyl]-7-oxabicyclo[2.2.1]hept-2-yl]-5-octenoic acid

A.

[1S-(1β,2α,3α,4β)]-3-[3-(Hydroxymethyl)-7-oxabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (XIII in reaction sequence C) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO4 and concentrated in vacuo. The solid residue was triturated with hexane (1 liter), filtered, and dried in vacuo to yield 220 g (100%) of desired compound (hemiacetal F in reaction sequence C), m.p. 104°–105° C., $[\alpha]_D = +27°$ c=1 MeOH.

TLC: Silica gel; EtOAc; $R_f$=0.3; Ce(SO4)2.

The above Wittig procedure was repeated on the hemiacetal F used in place of hemiacetal XIII to form the title aldehyde.

B.
[1S-[1β,2α(Z),3α,4β]]-8-[3-(Hydroxymethyl)-7-oxabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of Part A aldehyde 1.02 g (6 mmole) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 70 g of silica gel with 50/50 ethyl acetate-hexane as the eluant which gave 1.1 g of acid. This was treated with diazomethane (CH2N2) in Et2O to give the title compound.

C.
[1S-[1β,2α(Z),3α,4β]]-8-[3-[[[(Hexylamino)propyl]amino]methyl]-7-oxabicyclo[2.2.1]hept-2-yl]-5-octenoic acid Following the procedure of Examples 1 and 2 except substituting the title B ester for the ester used in Example 1 Part B, the title compound is obtained.

EXAMPLE 16

[1S-[1β,2α(Z),3α,4β]]-6-[3-[[(Hexylamino)acetyl]amino]methyl]-7-oxabicyclo[2.2.1]hept-2-yl]-1-(1H-tetrazol-5-yl)-4-hexane A.
[1S-[1β,2α(Z),3α,4β]]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO3 solution, washed with 100 ml of ether, acidified with dilute HCl to pH 3, and extracted with three 500 ml portions of ethyl acetate. The combined organic solutions are dried over anhydrous MgSO4, and purified by silica chromatography using a 5% methanol in methylene chloride eluant to provide 2 g of title A compound.

B.
[1S-[1β,2α(5Z),3α,4β]]-6-[3-[[(Hexylamino)propyl]amino]methyl]-7-oxabicyclo[2.2.1]hept-2-yl]-1-(1H-tetrazol-5-yl)-4-hexene Following the procedure of Examples 1 and 2 except substituting the Part A compound for the hydroxymethyl compound used in Example 1 Part B, the title compound is obtained.

EXAMPLE 17

[1S-[1β,2α(5Z),3α,4β]]-7-[3-[[[(Hexylamino)acetyl]amino]methyl]-7-oxabicyclo[2.2.1]hept-2-yl]-N-hydroxy-N-methyl-5-heptenamide A solution of Example 2 acid (0.82 mmole) in dry benzene (5.0 ml) is treated with oxalyl chloride (1 ml; 11.24 mmole or 13.7 eq.) and a drop of DMF, and stirred at room temperature under nitrogen for 2 hours.

The excess oxalyl chloride and solvent are blown off by a stream of nitrogen while heating the reaction flask in a warm water bath and the oil obtained dried in vacuo (oil pump) for 1 hour. The residual acid chloride is dissolved in dry tetrahydrofuran (1.5 ml) and added dropwise into a cold solution (0°, ice-water) of 98% methylhydroxylamine hydrochloride (139.8 mg; 1.64 mmole; 2 eq.) and triethylamine (0.34 ml; 2.46 mmole; 3 eq.) in tetrahydrofuran (2 ml) and water (2.0 ml). The mixture is stirred at 0° under nitrogen for 30 minutes and at room temperature for 5.5 hours, diluted with water (10 ml) and extracted twice with dichloromethane (50 ml). The organic extract is washed with 1N HCl (10 ml), 5% NaHCO₃ (5 ml) and water (10 ml), dried (anhydrous MgSO₄), filtered and evaporated to dryness giving the crude product, which is purified by silica gel column to afford the title compound.

EXAMPLE 18

[1S-[1β,2α(6Z),3α,4β]]-7-[3-[[[(Hexylamino)acetyl]amino]methyl]-7-oxabicyclo[2.2.1]hept-2-yl]-6-heptenoic acid

A.

[1S-[1β,2α(6Z),3α,4β]]-7-[3-(Hydroxymethyl)-7-oxabicyclo[2.2.1]hept-2-yl]-6-heptenoic acid, methyl ester A slurry of carboxypentyl triphenylphosphonium bromide in THF was cooled in an ice bath and treated dropwise with 1.4M KOt-amylate in toluene. After completion of this addition, the reaction mixture was allowed to warm to room temperature and was stirred for 6 hours. To this stirred solution was then added a solution of hemiacetal XIII (reaction sequence G) (prepared as described in Example 3 of U.S. Pat. No. 4,143,054) in THF dropwise over 30 minutes. The reaction mixture was then stirred overnight (15 hours). The mixture was cooled in an ice bath and quenched with HOAc. The solvent was removed in vacuo and the resulting residue was dissolved in saturated NaCl solution. This was extracted with chloroform. The chloroform layers were then extracted with saturated NaHCO₃ solution. The aqueous extracts were acidified to pH~3.5 by addition of aqueous HCl solution, and then were extracted with several portions of chloroform. The combined chloroform extracts were concentrated in vacuo to afford the crude product. The crude acid was esterified with excess ethereal diazomethane at 0° C. and then was purified by chromatography on silica gel to afford the title ester.

B.

[1S-[1β,2α(6Z),3α,4β]]-7-[3-[[[(Hexylamino)propyl]amino]methyl]-7-oxabicyclo[2.2.1]hept-2-yl]-6-heptenoic acid Following the procedure of Example 1 except substituting the Part A ester for the hydroxymethyl compound used in Example 1 Part B, the title compound is obtained.

EXAMPLE 19

[1S-[1β,2α(2E),3α,4β]]-7-[3-[[[(Hexylamino)acetyl]amino]methyl]-7-oxabicyclo[2.2.1]hept-2-yl]2-heptenoic acid

A.

[1S-(1β,2α,3α,4β)]-5-[3-(Hydroxymethyl)-7-oxabicyclo[2.2.1]hept-2-yl]pentanal

Following the procedure of Example 15 Part A, except substituting [1S-(1β,2α,3α,4β)]-3-[3-(hydroxymethyl)-7-oxabicyclo[2.2.1]hept-2-yl]propionaldehyde for the hemiacetal XIII (see reaction sequence C or E), [1S-(1β,2α,3α4β)]-4-[3-(hydroxymethyl)-7-oxabicyclo[2.2.1]hept-2-yl]butanal is obtained. Then by repeating the procedure of Example 15 Part A on [1S-(1β,2α,3α,4β)]-4-[3-(hydroxymethyl)-7-oxabicyclo[2.2.1]hept-2-yl]butanal, the title A aldehyde is produced.

B.

[1S-[1β,2α(2E),3α,4β]]-7-[3-(Hydroxymethyl)-7-oxabicycl[2.2.1]hept-2-yl]-2-heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title ester.

C.

[1S-[1β,2α(2E),3α,4β]]-7-[3-[[[(Hexylamino)propyl]amino]methyl]-7-oxabicyclo[2.2.1]hept-2-yl]-2-heptenoic acid Following the procedure of Example 1 except substituting the Part B ester for the ester used in Example 1 Part B, the title compound is obtained.

EXAMPLE 20

[1S-[1β,2α(5Z),3α,4β]]-7-[3-[(Methylamino)methyl]-7-oxabicyclo[2.2.1]hept-2-yl]-5-heptenoic acid, methyl ester Chiral amine from Example 1, Part C, (1 mmole) and N,N-dimethylformamide dimethylacetal (1.5 mmole) are dissolved in CH₂Cl₂ (6 ml). The reaction is stirred at room temperature overnight. The solvent and the excess reagent are evaporated to give crude amidine, which is dissolved in CH₂Cl₂ (5 ml). Methyl triflate (2 mmole) is added into the reaction at room temperature and the reaction is stirred for 1 hour at room temperature. The organic solvent and the excess reagent are evaporated off in vacuo and the residue is treated with methanolic hydrogen chloride at room temperature overnight. The reaction is concentrated in vacuo and the resulting crude product is dissolved in 1N HCl. The water layer is washed with ethyl ether and basified with saturated NaHCO₃. The water layer is extracted with ethyl ether, which is dried over MgSO₄. Filtration and evaporation of the solvent leave a crude product, which is purified by silica gel column to give the title compound.

The title compound is then employed in place of the chiral amine from Example 1 Part C to prepare compounds of the invention wherein R¹ is CH₃.

EXAMPLES 21 TO 48

Following the procedures outlined in the specification and described in the above working Examples, the following compounds may be prepared.

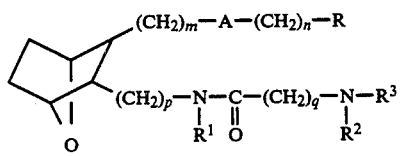

| Ex. No. | m | A | $(CH_2)_n$ | R | p | $R^1$ | $(CH_2)_q$ | $R^2$ | $R^3$ |
|---|---|---|---|---|---|---|---|---|---|
| 21 | 2 | CH=CH | $CH_2$ | $CO_2H$ | 1 | H | $(CH_2)_2$ | $CH_3$ | H |
| 22 | 3 | $(CH_2)_2$ | $(CH_2)_2$ | $CH_2OH$ | 2 | $C_2H_5$ | $(CH_2)_3$ | H | $CH_3$ |
| 23 | 4 | CH=CH | $(CH_2)_3$ | $\begin{array}{c}N-N\\ \diagdown \diagup \\ \text{(triazole)} \\ N \\ | \\ H\end{array}$ | 3 | H | $(CH_2)_4$ | H | $-CH_2CH=CH-CH_3$ |
| 24 | 1 | $(CH_2)_2$ | $(CH_2)_4$ | $\underset{\|}{O}=\underset{\|}{C}N(CH_3)C_2H_5$ | 1 | $CH_3$ | $(CH_2)_5$ | $CH_3$ | $-CH_2-C\equiv C-CH_3$ |
| 25 | 0 | CH=CH | $(CH_2)_5$ | $\underset{\|}{O}=\underset{\|}{C}N-OH\ \ CH_3$ | 2 | H | $(CH_2)_6$ | $C_2H_5$ | $-CH_2-CH_2-C\equiv C-CH_3$ |
| 26 | 2 | CH=CH | $\begin{array}{c}CH_3\\ \|\\ -CH-\\ \|\\ CH_3\end{array}$ | $\underset{\|}{O}=\underset{\|}{C}N-OCH_3\ \ H$ | 3 | $C_2H_5$ | $(CH_2)_7$ | $C_3H_7$ | $\begin{array}{c}H\ \ H\\ \|\ \ \|\\ -CH_2-CH_2-C=C-CH_3\end{array}$ |
| 27 | 3 | $(CH_2)_2$ | $\begin{array}{c}CH_3\\ \|\\ -C-\\ \|\\ CH_3\end{array}$ | $\underset{\|}{O}=\underset{\|}{C}N-OC_2H_5\ \ CH_3$ | 4 | H | $\begin{array}{c}CH_3\\ \|\\ -CH-\end{array}$ | $C_4H_9$ | $-C_6H_5$ |
| 28 | 4 | $(CH_2)_2$ | $(CH_2)_4$ | $\underset{\|}{O}=\underset{\|}{C}NHC_6H_5$ | 1 | $C_3H_7$ | $-CH_2-$ | $C_5H_{11}$ | $-C_6H_5$ |
| 29 | 1 | CH=CH | $\begin{array}{c}CH_3\ \ CH_3\\ \ \ \diagdown\diagup\\ \ \ \ C\\ \diagup\ \diagdown\\ -CH_2\ \ CH_2-\end{array}$ | $CO_2Li$ | 2 | H | $\begin{array}{c}CH_3\\ \|\\ -CH_2-CH\\ \|\\ CH_3\end{array}$ | H | $CH_2C_6H_5$ |
| 30 | 0 | CH=CH | $\begin{array}{c}CH_3\ CH_3\\ \|\ \ \ \|\\ -CH-CH-\end{array}$ | $CO_2Na$ | 3 | $CH_3$ | $\begin{array}{c}CH_3\ CH_3\\ \diagdown\ \diagup\\ C\\ \diagup\diagdown\\ -CH_2\ \ CH_2-\end{array}$ | H | $-(CH_2)_2C_6H_5$ |
| 31 | 1 | $(CH_2)_2$ | $\begin{array}{c}CH_3\\ \|\\ -C-\\ \|\\ F\end{array}$ | $CO_2$ glucamine salt | 4 | $C_2H_5$ | $\begin{array}{c}CH_3\\ \|\\ -CH_2-CH-CH_2-\end{array}$ | H | $-C_6H_4-p-CH_3$ |
| 32 | 2 | CH=CH | $\begin{array}{c}F\ \ \ F\\ \|\ \ \ \|\\ -CH-CH-\end{array}$ | $CO_2$ tris salt | 1 | H | $-(CH_2)_3-$ | $CH_3$ | $-C_6H_4-p-OH$ |

-continued

| Ex. No. | m | A | (CH₂)ₙ | R | p | R¹ | (CH₂)q | R² | R³ |
|---|---|---|---|---|---|---|---|---|---|
| 33 | 3 | (CH₂)₂ | -C(F)(CH₂-)- (F, CH₂) | CH₂OH | 2 | C₄H₉ | -CH₂-CH(C₂H₅)- | CH₃ | -OCH₃ |
| 34 | 4 | (CH₂)₂ | -(CH₂)₅- | (triazole: N=N, N-N-H, CH₃) | 3 | H | -CH₂-C(CH₃)(H)-CH₂- | CH₃ | -OC₂H₅ |
| 35 | 0 | CH=CH | -CH₂-CH(CH₃)-CH₂- | O=C-NH₂ | 4 | CH₂ | -C(CH₃)(CH₃)-CH₂- (‑C(CH₃)₂‑) | C₂H₅ | -OCH₂C₆H₅ |
| 36 | 0 | (CH₂)₂ | -CH₂-C(CH₃)(CH₃)- | O=C-N(H)-OH | 1 | C₂H₅ | (CH₂)₂ | CH₃ | cyclopentyl |
| 37 | 1 | CH=CH | CH₂ | O=C-N(CH₃)₂ | 2 | H₅ | -CH₂- | H | cyclohexyl |
| 38 | 2 | (CH₂)₂ | (CH₂)₂ | O=C-N(CH₃)-OH | 3 | CH₃ | -CH₂-C(CH₃)(CH₃)- | C₄H₉ | -CH₂-cyclohexyl |
| 39 | 3 | CH=CH | (CH₂)₃ | CO₂H | 4 | C₂H₅ | -CH₂-CH(CH₃)-CH(CH₃)-CH₂- | CH₃ | -OCH₂-phenyl |
| 40 | 4 | (CH₂)₂ | (CH₂)₄ | CH₂OH | 1 | C₃H₇ | (CH₂)₂ | C₂H₅ | -C₇H₅ |
| 41 | 0 | CH=CH | -CH₂C(F)(F)- | (triazole: N=N, N-N-H, CH₃) | 2 | C₄H₉ | (CH₂)₃ | CH₃ | H |

-continued

| Ex. No. | m | A | $(CH_2)_n$ | R | p | $R^1$ | $(CH_2)_q$ | $R^2$ | $R^3$ |
|---|---|---|---|---|---|---|---|---|---|
| 42 | 1 | $(CH_2)_2$ | $\begin{array}{c}CH_3\\ \mid\\ -CH_2-C-\\ \mid\\ CH_3\end{array}$ | $\underset{\parallel}{\overset{O}{C}}N(C_2H_5)_2$ | 3 | $C_5H_{11}$ | $\begin{array}{c}F\\ \mid\\ -CH-CH_2-\end{array}$ | $C_3H_7$ | $C_4H_9$ |
| 43 | 2 | CH=CH | $(CH_2)_5$ | $\underset{\parallel}{\overset{O}{C}}NHC_6H_5$ | 4 | H | $\begin{array}{c}F\quad F\\ \diagdown\;\diagup\\ -C-CH_2-\end{array}$ | $C_4H_9$ | $-(CH_2)_2CH=CHCH_3$ |
| 44 | 3 | $(CH_2)_2$ | $\begin{array}{c}CH_3\;F\\ \mid\;\;\mid\\ -CH_2-CH-\end{array}$ | $CH_2OH$ | 1 | H | $(CH_2)_2$ | H | $C_6H_5$ |
| 45 | 4 | $(CH_2)_2$ | $(CH_2)_2$ | $\begin{array}{c}N=N\\ \diagup\;\;\;\diagdown\\ \diagdown\;\;\;\diagup\\ N-N\\ \mid\\ H\end{array}$ | 2 | H | $CH_2$ | H | $-CH_2C_6H_5$ |
| 46 | 0 | CH=CH | $(CH_2)_3$ | $CO_2CH_3$ | 3 | $CH_3$ | $(CH_2)_3$ | $C_3H_7$ | $-OC_4H_9$ |
| 47 | 2 | $(CH_2)_2$ | $(CH_2)_4$ | $CO_2CH_3$ | 4 | $CH_3$ | $(CH_2)_8$ | H | $-OCH_2C_6H_5$ |
| 48 | 3 | CH=CH | $(CH_2)_5$ | $CO_2H$ | 1 | $CH_3$ | $(CH_2)_{10}$ | H | $-CH(CH_3)(C_6H_5)$ |

What is claimed is:

1. A compound having the structure

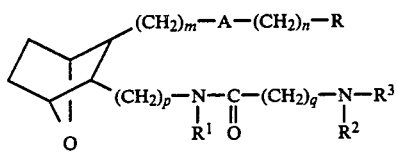

including all stereoisomers thereof, wherein m is 0 to 4; A is —CH=CH— or —CH$_2$—CH$_2$—; n is 1 to 5; R is CO$_2$H, CO$_2$alkyl, CO$_2$alkali metal, CO$_2$polyhydroxyamine salt, —CH$_2$OH,

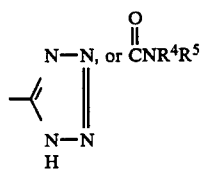

wherein R$^4$ and R$^5$ are the same or different and are H, lower alkyl, hydroxy, lower alkoxy or aryl at least one of R$^4$ and R$^5$ being other than hydroxy and lower alkoxy; p is 1 to 4; R$^1$ is H or lower alkyl; q is 1 to 12; R$^2$ and R$^3$ may be the same or different and are H, lower alkyl, lower alkenyl containing 2 to 12 carbons, lower alkynyl containing 2 to 12 carbons, aryl, arylalkyl, lower alkoxy, aralkyloxy, cycloalkyl or cycloalkylalkyl, wherein lower alkyl or alkyl alone or as part of another group contains 1 to 12 carbons and is unsubstituted or is substituted with halo, CF$_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;

aryl alone or as part of another group contains 6 to 10 carbons in the ring portion and is unsubstituted or is substituted with 1 or 2 lower alkyl groups, 1 or 2 halogens, 1 or 2 hydroxy groups, 1 or 2 lower alkoxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups; and cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defined in claim 1 wherein R$^2$ is H and R$^3$ is alkyl.

3. The compound as defined in claim 1 wherein A is CH=CH.

4. The compound as defined in claim 1 wherein m is 1 and n is 1 to 4.

5. The compound as defined in claim 1 wherein p is 1 and q is 1.

6. The compound as defined in claim 1 wherein R is CO$_2$alkyl or CO$_2$H.

7. The compound as defined in claim 1 wherein R$^1$ is H and R$^2$ is H or CH$_3$ and R$^3$ is C$_4$H$_9$, C$_5$H$_{11}$, C$_6$H$_{13}$, C$_7$H$_{15}$, C$_6$H$_5$,

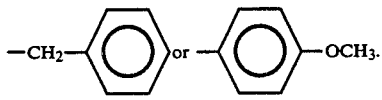

8. The compound as defined in claim 1 wherein m is 1, n is 2 to 4, R is CO$_2$alkyl, CO$_2$H, CH$_2$OH, or

p is 1, R$^1$ is H, q is 1, R$^2$ is H or alkyl and R$^3$ is alkyl or alkoxyphenyl.

9. The compound as defined in claim 1 having the name [1S-[1β,2α(5Z),3α,4β]]-7-[3-[[[(4-methoxyphenyl)acetyl]amino]methyl]-7-oxabicyclo[2.2.1]hept-2-yl]-5-heptenoic acid or esters thereof, including all stereoisomers thereof.

10. The compound as defined in claim 1 having the name [1S-[1β,2α(5Z),3α,4β]]-7-[3-[[[(hexylamino)acetyl]amino]methyl]-7-oxabicyclo[2.2.1]hept-2-yl]-5-heptenoic acid or esters thereof, including all stereoisomers thereof.

11. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 0.1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation which comprises administering to a mammalian host an effective amount of a compound as defined in claim 1 or a pharmaceutically acceptable salt thereof.

15. A method of inhibiting bronchoconstriction associated with asthma, which comprises administering to a mammalian host an effective amount of a compound as defined in claim 1 or a pharmaceutically acceptable salt thereof.

16. A method of treating peripheral vascular diseases, which comprises topically or systemically administering to a mammalian host an effective amount of a compound as defined in claim 1 or a pharmaceutically acceptable salt thereof.

* * * * *